(12) United States Patent
Bolos

(10) Patent No.: US 10,479,600 B2
(45) Date of Patent: Nov. 19, 2019

(54) PRE-LOADED WASTE BAG SYSTEMS AND METHODS

(71) Applicant: Dear Future Me LLC, Chicago, IL (US)

(72) Inventor: Michael F. Bolos, Burr Ridge, IL (US)

(73) Assignee: Dear Future Me, LLC, Chicago, IL (US)

( * ) Notice: Subject to any disclaimer, the term of this patent is extended or adjusted under 35 U.S.C. 154(b) by 97 days.

(21) Appl. No.: 15/491,992

(22) Filed: Apr. 20, 2017

(65) Prior Publication Data

US 2017/0305662 A1   Oct. 26, 2017

Related U.S. Application Data

(60) Provisional application No. 62/325,247, filed on Apr. 20, 2016.

(51) Int. Cl.

| | |
|---|---|
| *B65F 1/06* | (2006.01) |
| *B65D 33/28* | (2006.01) |
| *B65F 1/14* | (2006.01) |
| *A61L 9/12* | (2006.01) |
| *B65F 1/00* | (2006.01) |

(52) U.S. Cl.
CPC .............. *B65F 1/062* (2013.01); *A61L 9/12* (2013.01); *B65D 33/28* (2013.01); *B65F 1/002* (2013.01); *B65F 1/06* (2013.01); *B65F 1/14* (2013.01); *B65F 2210/129* (2013.01); *B65F 2250/00* (2013.09)

(58) Field of Classification Search
CPC ....................................................... B65F 1/062
See application file for complete search history.

(56) References Cited

U.S. PATENT DOCUMENTS

| | | | | |
|---|---|---|---|---|
| 3,888,406 | A * | 6/1975 | Nippes ..................... | B65F 1/062 206/554 |
| 5,803,299 | A * | 9/1998 | Sealy, Jr. ................ | B65F 1/062 220/495.07 |
| 6,808,073 | B2 | 10/2004 | Cruisinier | |
| 2003/0089719 | A1 | 5/2003 | Berger | |

* cited by examiner

*Primary Examiner* — Stephen J Castellano
(74) *Attorney, Agent, or Firm* — Barich IP Law Group

(57) ABSTRACT

One or more embodiments provide a pre-loaded waste bag system comprised of a plurality of disposable, drawstring waste bags nested one inside the other. The waste bin is comprised of a rigid frame containing two pairs of securing members molded into or affixed to opposite sides of the outside of the waste bin walls. The waste bags are placed inside the waste bin, with the drawstrings looped around the securing members located on the waste bin. The innermost bag is removed by sliding the drawstring of the innermost bag off of the securing members and pulling the innermost bag out of the waste bin. The action separates two sheets of a releasable, scented square releasing a pleasant odor or perfume contained within the two sheets.

6 Claims, 6 Drawing Sheets

PRE-LOADED WASTE BAG SYSTEMS AND METHODS

CROSS-REFERENCE TO RELATED APPLICATIONS

The present application claims the benefit of U.S. Provisional Application No. 62/325,247, filed Apr. 20, 2016, entitled "PRE-LOADED WASTE BAG SYSTEMS AND METHODS", which is hereby incorporated by reference in its entirety.

BACKGROUND OF THE INVENTION

The present invention generally relates to a waste bag system. More particularly, the present invention generally relates to a waste bag system that engages with a waste bin.

Prior art waste bags are typically sold as a roll of individual waste bags. An individual waste bag is detached from the roll and positioned by a user in a waste bin. Once the waste bag is full, the waste bag is removed from the waste bin by the user and a new waste bag is detached from the roll and positioned in the waste bin. Unfortunately, such a process can be time consuming and potentially messy if a bag failure occurs.

Two prior art systems have attempted to develop a waste bag system that includes waste bags nested inside each other that are positionable at the same time inside a waste bin.

The first prior art attempt is found in U.S. Pat. App. Publication No. 2003/0089719 to Berger entitled "Garbage Bag System". Berger shows a garbage bag system including several nested bags that are attached to a trash bin with a securing system. Unfortunately, Berger teaches that the bags are perforated and are separated from each other by tearing along a perforation. Unfortunately, such a system is prone to bag ripping and does not provide a convenient way to close the bag once it is detached from the other bags.

The second prior art system is U.S. Pat. No. 6,808,073 to Cuisinier entitled "Bag Assembly". Cuisinier also shows a trash bag system including several nested bags. However, Cuisinier does not teach any way of securely engaging the nested bags with the trash bin. Consequently, the weight of the nested bags may cause the bags to undesirably slide into the interior of the trash bin.

BRIEF SUMMARY OF THE INVENTION

A pre-loaded waste bag system and method is presented that includes a set of pre-loaded waste bags that include drawstrings and a waste bin including a plurality of drawstring securing members. The pre-loaded waste bags are introduced into the waste bin and the drawstrings are engaged with the drawstring securing members. This causes the pre-loaded waste bags to tighten along the upper perimeter of the waste bin and engage with a bag hem engagement structure of the waste bin. Individual bags may be disengaged from the drawstring securing members and removed from the waste bin as desired, but the remaining bags maintain engagement with the waste bin.

Additionally, a scent strip is positioned between two or more of the bags in the set of pre-loaded waste bags. As an inner bag is removed, it de-adheres an adhesive in the scent strip to expose a scent element and release a scent.

DETAILED DESCRIPTION OF THE INVENTION

Figure 1:
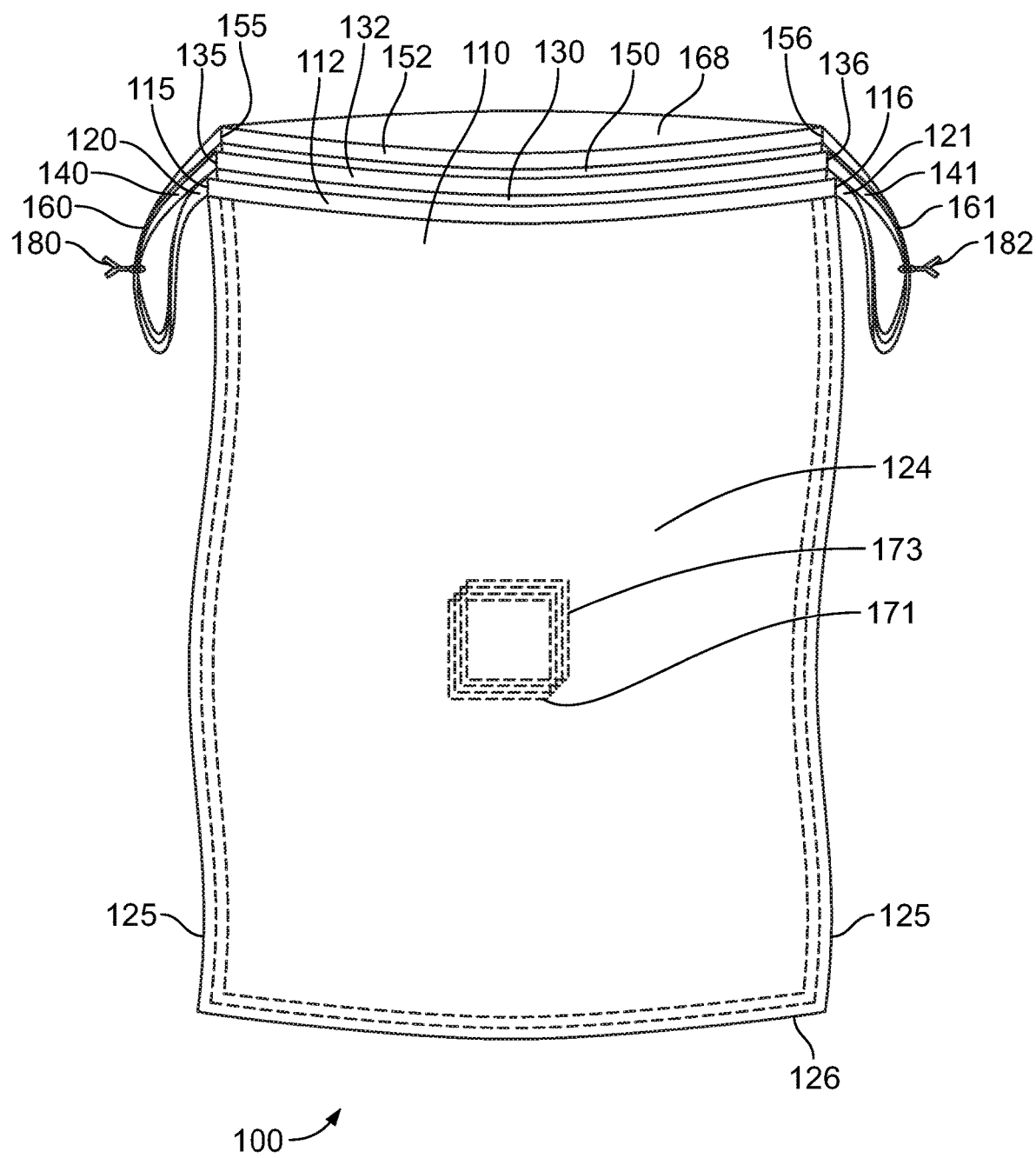
FIG. 1 illustrates a set of pre-loaded waste bags according to an embodiment of the present invention.

FIG. 1 illustrates a set of pre-loaded waste bags 100 according to an embodiment of the present invention. As shown in FIG. 1, the set of pre-loaded waste bags 100 includes an exterior bag 110, a medial bag 130, and an interior bag 150.

The exterior bag 110 includes an exterior bag tubular hem 112. The exterior bag tubular hem 112 includes an exterior bag first drawstring opening 115 and an exterior bag second drawstring opening 116. An exterior bag first drawstring 120 is positioned within the exterior bag tubular hem 112 and extends through the exterior bag first drawstring opening 115. An exterior bag second drawstring 121 is positioned within the exterior bag tubular hem 112 and extends through the exterior bag second drawstring opening 116.

The exterior bag 110 is composed of an exterior bag front wall 124 and an exterior bag back wall (not shown). The exterior bag front wall 124 and the exterior bag back wall are joined at the exterior bag side wall seams 125 and exterior bag bottom seam 126.

The exterior bag 110 includes both an exterior bag outer side (shown) and exterior bag inner side (not shown) which is disposed in the interior of the exterior bag. As further described below, one side of a releasable exterior bag-medial bag scent strip 170 is affixed on the exterior bag inner side. Although not visible from the outer side of the exterior bag, the location 171 of the exterior bag-medial bag scent strip is shown in FIG. 1 in dotted lines.

The medial bag 130 includes a medial bag tubular hem 132. The medial bag tubular hem 132 includes a medial bag first drawstring opening 135 and a medial bag second drawstring opening 136. A medial bag first drawstring 140 is positioned within the medial bag tubular hem 132 and extends through the medial bag first drawstring opening 135. A medial bag second drawstring 141 is positioned within the medial bag tubular hem 132 and extends through the medial bag second drawstring opening 136.

The medial bag 130 is composed of a medial bag front wall 144 (not shown) and a medial bag back wall (not shown). The medial bag front wall and the medial bag back wall are joined at the medial bag side wall seams 145 and medial bag bottom seam 146. Although the medial bag side wall seams 145 and medial bag bottom seam 146 are not visible from the outer side of the pre-loaded waste bags 100, the location of the medial bag side wall seams 145 and medial bag bottom seam 146 are shown in FIG. 1 in dotted lines.

The medial bag 130 includes both a medial bag outer side (not shown) and medial bag inner side (not shown) which is disposed in the interior of the medial bag. As further described below, one side of the releasable exterior bag-medial bag scent strip 170 is affixed on the medial bag outer side. As further described below, the portion of the exterior bag-medial bag scent strip 170 that is positioned on the medial bag outer side is adhered to the portion of the exterior bag-medial bag scent strip 170 that is positioned on the exterior bag inner side. Although not visible from the outer side of pre-loaded waste bags 100, the location 171 of the exterior bag-medial bag scent strip 170 is shown in FIG. 1 in dotted lines.

Additionally, the medial bag 130 includes one side of a releasable medial bag-interior bag scent strip 172 affixed on the medial bag inner side. As further described below, the portion of the medial bag-interior bag scent strip 172 that is positioned on the medial bag inner side is adhered to the portion of the medial bag-interior bag scent strip 172 that is positioned on the interior bag outer side. Although not visible from the outer side of pre-loaded waste bags 100, the location 173 of the medial bag-interior bag scent strip 172 is shown in FIG. 1 in dotted lines.

The interior bag 150 includes an interior bag tubular hem 152. The interior bag tubular hem 152 includes an interior bag first drawstring opening 155 and an interior bag second drawstring opening 156. An interior bag first drawstring 160 is positioned within the interior bag tubular hem 152 and extends through the interior bag first drawstring opening 155. An interior bag second drawstring 161 is positioned within the interior bag tubular hem 152 and extends through the interior bag second drawstring opening 156.

The interior bag 150 is composed of an interior bag front wall 164 (not shown) and an interior bag interior wall 168 that also describes the interior of the pre-loaded waste bags 100. The interior bag front wall 164 and the interior bag interior wall 168 are joined at the interior bag side wall seams 165 and interior bag bottom seam 166.

The interior bag 150 includes both an interior bag outer side (not shown) and interior bag inner side 168 which is disposed in the interior of the interior bag. As further described below, one side of a releasable medial bag-interior bag scent strip 172 is affixed on the interior bag outer side. Although not visible from the outer side of the pre-loaded waste bags 100 the location 173 of the interior bag-interior bag scent strip is shown in FIG. 1 in dotted lines.

As shown in FIG. 1, the exterior bag first drawstring 115, medial bag first drawstring 135, and interior bag first drawstring 155 are joined together by a first drawstring joining member 180. Further, the exterior bag second drawstring 116, medial bag second drawstring 136, and interior bag second drawstring 156 are joined together by a second drawstring joining member 182.

Although the embodiment of FIG. 1 only shows a single medial bag 130, a greater number of medial bags may be positioned inside each other between the exterior bag 110 and interior bag 150. For example, there may be two or ten medial bags positioned inside each other.

Additionally, one or more of the exterior, medial or interior bags may be adhered to each other in whole or in part. For example one or more of the bags may include one or more adhesive regions positioned on its hem to join the bag to another bag.

Additionally, on one embodiment, one or more of the exterior, medial or interior bags may omit the scent strip. Further, in an embodiment including multiple medial bags, the scent strip may alternatively be positioned between every other bag instead of between every bag.

Also, in an alternative embodiment, one or more of the exterior, medial or interior bags may be manufactured without one or both of the side seams and bottom seam.

Figure 2:
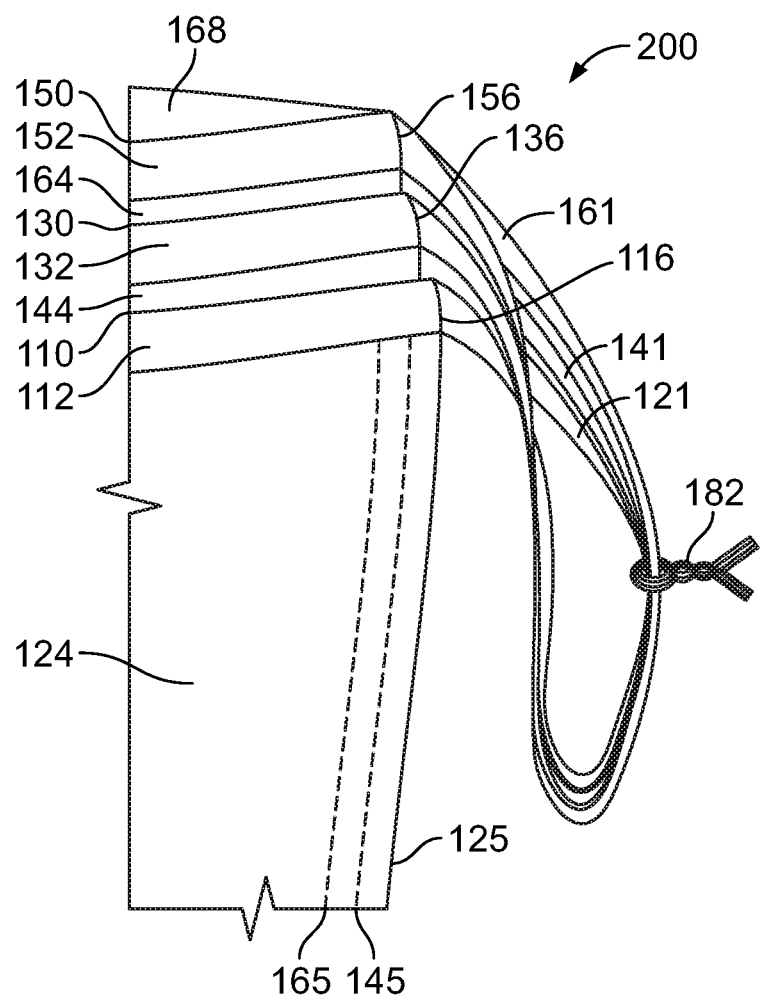
FIG. 2 illustrates a close-up view of the drawstrings of the set of pre-loaded waste bags of FIG. 1 showing the drawstrings of the exterior, medial, and interior bags exiting the second drawstring opening.

FIG. 2 illustrates a close-up view of the drawstrings of the set of pre-loaded waste bags 100 of FIG. 1 showing the drawstrings of the exterior, medial, and interior bags exiting the second drawstring opening. More specifically, FIG. 2 shows the exterior bag 110, exterior bag tubular hem 112, exterior bag second drawstring opening 116, exterior bag second drawstring 121, exterior bag front wall 124, exterior bag side wall seams 125, the medial bag 130, medial bag tubular hem 132, medial bag second drawstring opening 136, medial bag second drawstring 141, medial bag front wall 144, medial bag side wall seam location 145, the interior bag 150, interior bag tubular hem 152, interior bag second drawstring opening 156, interior bag second drawstring 161, interior bag front wall 164, interior bag side wall seam location 165, and the interior bag interior wall 168, and the second drawstring joining member 182.

As shown in FIG. 2, the drawstring joining member may be a twist tie. Alternatively, as further discussed below in FIG. 14-15, the drawstring joining member may be a thermally adhered clamp.

Alternatively, the joining member may be an adhesive that is positioned between one or more of the exterior, medial, and/or interior drawstrings. Alternatively, one or more of the exterior, medial, and/or interior drawstrings may be joined together by a structural element having perforations that may be torn to separate the drawstrings.

Figure 3:
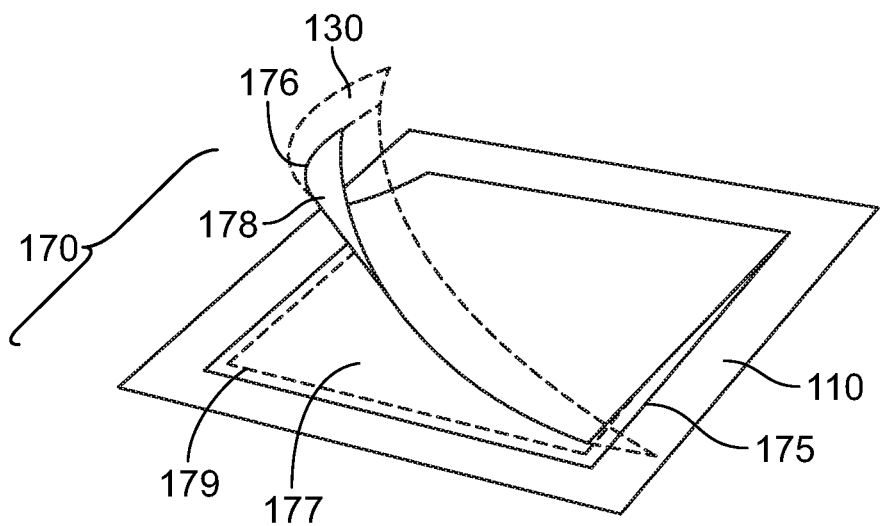
FIG. 3 illustrates a cutaway view of the exterior bag-medial bag scent strip.

FIG. 3 illustrates a cutaway view of the exterior bag-medial bag scent strip 170. More specifically, FIG. 3 shows the exterior bag 110, medial bag 130, an exterior bag side 175 of the releasable exterior bag-medial bag scent strip, a medial bag side 176 of the releasable exterior bag-medial bag scent strip, an exterior bag side scent region 177, an interior bag side scent region 178, and a scent strip seal 179.

In one embodiment, a scent-bearing substance such as a gel, liquid, or paste may be positioned between the exterior bag side 175 and the medial bag side 176 and the exterior and medial bag sides may be sealed into place at the scent strip seal 179 to form a volume to contain the scent-bearing substance. The adhesive used for adhere the exterior bag side 175 and medial bag side 176 together at the scent strip seal 179 is less than the tensile strength of the exterior and medial bags. Consequently, once the medial bag 130 has filled with trash and a user seeks to remove the medial bag to dispose of it, the lifting action of the user induces a force between the exterior bag side 175 and the medial bag side 176 that causes the scent strip seal 179 to de-adhere or release, thus exposing the scent bearing substance.

In another embodiment, the scent strip may be preformed of two sheets of material with a scent bearing substance between them having adhesive exterior sides. The adhesive exterior sides may then be adhered to the exterior bag side and the interior bag side and operate generally as described above.

Alternatively, one or both of the exterior bag side scent region 177 and interior bag side scent region 178 may be composed of a scent-absorbing material that may release the scent when exposed.

In another embodiment an additional substance such as a germ killing agent and/or antimicrobial such as Lysol® may be included in the scent strip in addition to or instead of the scent.

Alternatively, in an embodiment where the scent strip is composed of two sheets of material with the scent bearing substance between them, only one of the sheets may have an adhesive on its exterior side and adhere to one of the bag sides. The other side sheet of the scent strip may be manually detachable, for example by using a pull tab.

Additionally, although the above scent strip is shown as having a generally square shape, the scent strip may be another shape such as rectangular, ovoid or circular. Additionally, more than one scent strip may be positioned between two bag surfaces. For example, a scent strip may be positioned on both the front wall and back wall of a bag.

Additionally, although the exterior bag-medial bag scent strip 170 is shown, the medial bag-interior bag scent strip 172 may be generally similar in shape or operation as described above.

Figure 4:
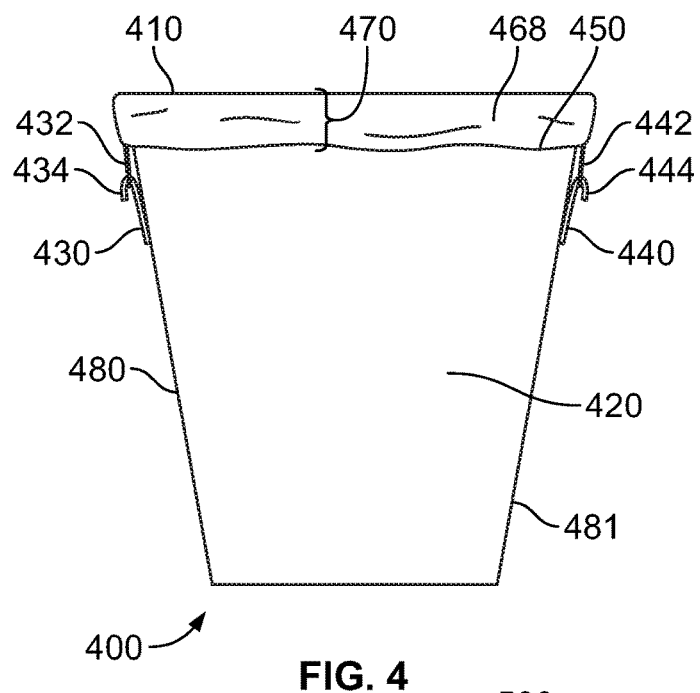
FIG. 4 illustrates a pre-loaded waste bag system according to an embodiment of the present invention.

FIG. 4 illustrates a pre-loaded waste bag system according to an embodiment of the present invention. The pre-loaded waste bag system 400 includes a set of pre-loaded waste bags 410 and a waste bin 420. The set of pre-loaded waste bags 410 include a first set of drawstrings 432 including the exterior bag first drawstring 120, medial bag first drawstring 140, and interior bag first drawstring 160 and a second set of drawstrings 442 including the exterior bag second drawstring 121, medial bag second drawstring 141, and interior bag second drawstring 161. Also shown are the bag hems 450 including the exterior bag tubular hem 112, medial bag tubular hem 132, and interior bag tubular hem 152, as well as the interior bag interior wall 468.

The waste bin 420 includes a bag hem engagement structure 470. Additionally, attached to the first exterior side 480 of the waste bin 420 is a first drawstring securing member 430 including a first drawstring engagement structure 434 that engages the first set of drawstrings 432. Also, attached to the second exterior side 481 of the waste bin 420 is a second drawstring securing member 440 including a second drawstring engagement structure 434 that engages the second set of drawstrings 432.

In operation, the set of pre-loaded waste bags 410 are introduced into the interior of the waste bin 420 and the first set of drawstrings 432 is engaged with the first drawstring engagement structure 434 and the second set of drawstrings 442 is engaged with the second drawstring engagement structure 444.

Additionally, the bag hem engagement structure 470 is constructed so that the top exterior edge of the waste bin 420 has a greater outward horizontal extent than the walls of the waste bin 420 below the top edge. Also, the distance of first and second drawstring engagement structures 434, 444 and the length of the first and second set of drawstrings 432, 442 have been designed so that when the drawstrings engage the engagement structure, the drawstrings are pulled taught around the exterior of the waste bin 420. Once the drawstrings are pulled taught around the exterior of the waste bin 420 and engaged with the engagement structures, adding heavy items to the interior of the set of pre-loaded waste bags 410 will not cause the set of pre-loaded waste bags 410 to become disengaged with the waste bin 420. Instead, heavy items will merely push the set of pre-loaded waste bags 410 downward into the interior of the waste bin 420, which will place a force on the drawstrings. However, the drawstrings are secured to the drawstring engagement structures, so additional force applied to the drawstrings merely causes the drawstrings to tighten and the bag hems 450 to contract around the exterior of the waste bin 420. Further, the tightened drawstrings are prevented from significant upward movement by engagement with the bag hem engagement structure 470.

In one embodiment, one or more of the drawstring engagement structures 434, 444 may be composed of one or more hook structures as shown in FIG. 4.

Figure 5:
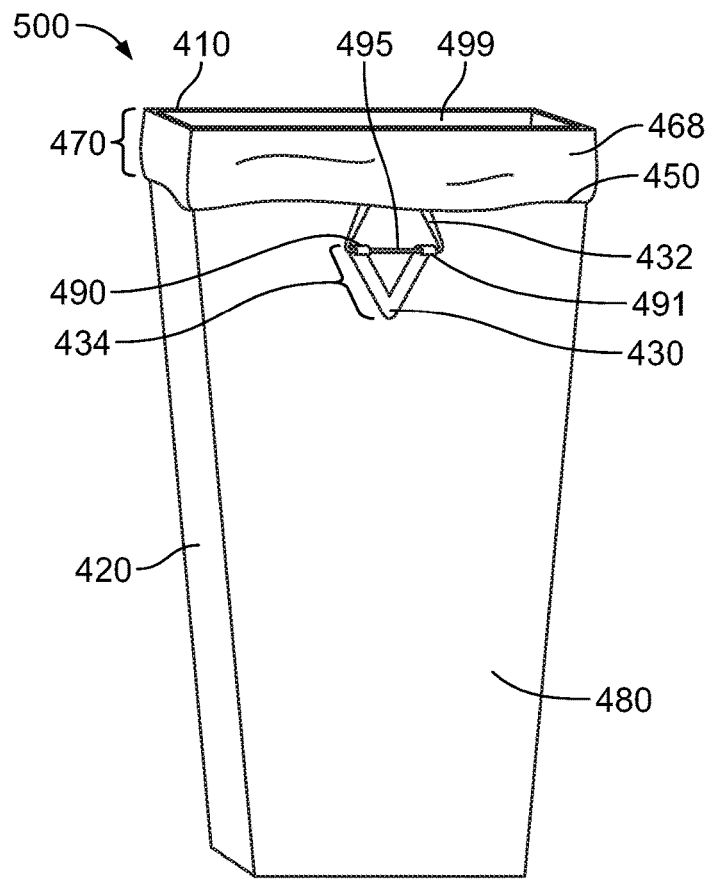
FIG. 5 illustrates a side view of an embodiment of the pre-loaded waste bag system of FIG. 4.

FIG. 5 illustrates a side view 500 of an embodiment of the pre-loaded waste bag system 400 of FIG. 4. FIG. 5 shows the waste bin 420 including the first exterior side 480, the bag hem engagement structure 470, a waste bin interior 499, and the first drawstring securing member 430. The set of pre-loaded waste bags 410 including the bag hems 450, interior bag interior wall 468, and first set of drawstrings 432. As shown in FIG. 5, the first drawstring engagement structure 434 includes a first hook-shaped structure 490 and a second hook shaped structure 491. The portion of the first set of drawstrings 432 extending between the first hook-shaped structure 490 and the second hook shaped structure 491 forms a drawstring grasping region 495.

In operation, the set of pre-loaded waste bags 410 is installed in the waste bin 420 by engaging the drawstrings 432 with the drawstring engagement structure 434. The drawstring grasping region 495 forms a convenient area for users to easily grasp the desired drawstring of innermost bag of the set of pre-loaded waste bags 410 while the remaining drawstrings remain engaged with the drawstring engagement structure 434.

Additionally, as mentioned above, drawstrings that remain engaged with the drawstring engagement structure 434 cause the hems of their respective bags to remain taught around the exterior of the waste bin 420 and thus engage with the bag hem engagement structure 470 of the waste bin 420 to prevent the bags from being removed from the waste bin 420.

Consequently, as a user removes an inner waste bag, the one or more of the sides of the waste bag may be adhered to the one or more sides of the next subsequent waste bag at a scent strip as described above. However, due to the engagement of the drawstrings with the drawstring engagement structure 434, as the interior bag is removed, the next subsequent bag is maintained in the interior 499 of the waste bin 420 even though it is adhered to the bag being removed. Further, the engagement provided between the waste bag and the waste bin 420 is such that it is greater than the adhesive force adhering the portion of the scent strip on the waste bag being removed to the portion of the sent strip on the next subsequent waste bag, which consequently causes the scent strip portions to de-adhere and expose the scent-bearing substance.

Figure 6:
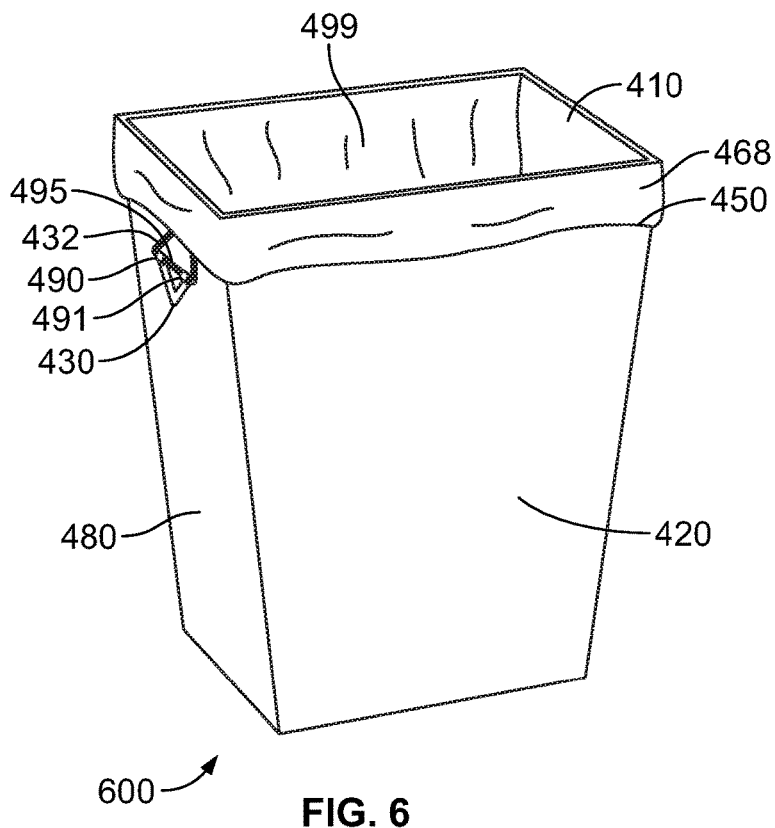
FIG. 6 illustrates a side view of the pre-loaded waste bag system of FIG. 5.

FIG. 6 illustrates a side view 600 of the pre-loaded waste bag system of FIG. 5. FIG. 6 shows the waste bin 420 including the first exterior side 480, the waste bin interior 499, and the first drawstring securing member 430. The set of pre-loaded waste bags 410 including the bag hems 450, interior bag interior wall 468, and first set of drawstrings 432. The first hook-shaped structure 490, second hook shaped structure 491, and drawstring grasping region 495 are also shown.

Figure 7:
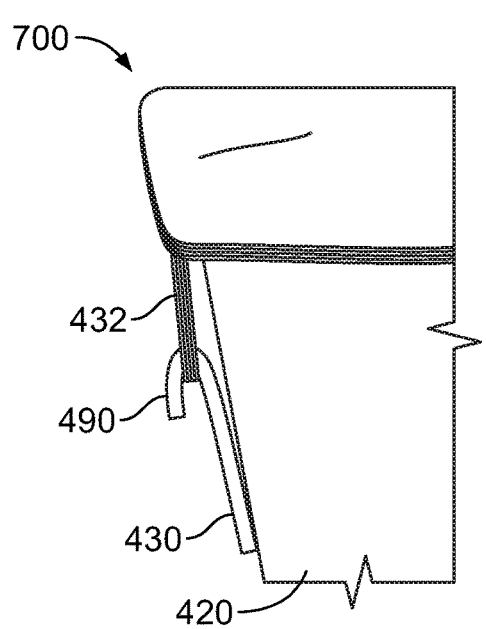
FIG. 7 illustrates a close-up side view of the engagement of the first set of drawstrings with the first hook shaped structure of the first drawstring securing member on the waste bin.

FIG. 7 illustrates a close-up side view 700 of the engagement of the first set of drawstrings 432 with the first hook shaped structure 490 of the first drawstring securing member 430 on the waste bin 420.

Figure 8:
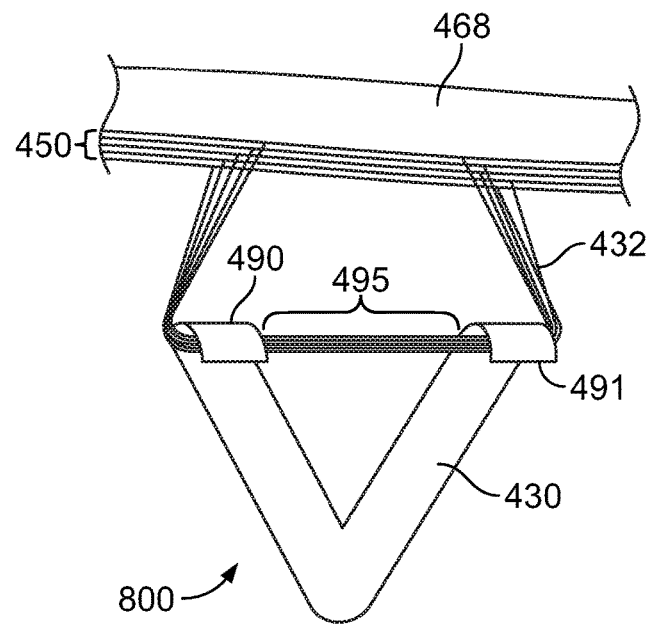
FIG. 8 illustrates a close-up front view of the engagement of the first set of drawstrings with the first hook shaped structure of the first drawstring securing member on the waste bin.

FIG. 8 illustrates a close-up front view 800 of the engagement of the first set of drawstrings 432 with the first hook shaped structure 490 of the first drawstring securing member 430 on the waste bin 420. Also shown are bag hems 450 and interior bag interior wall 468. The drawstring grasping region 495 is also shown.

FIGS. 9-13 illustrated alternative embodiments of the drawstring securing members.

Figure 9:
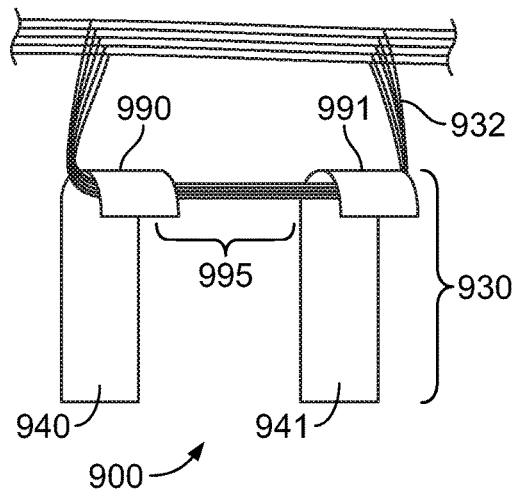
FIG. 9 illustrates an alternative embodiment of a drawstring securing member composed of a first securing member element including a first hook shaped structure and a second securing member element including a second hook-shaped structure.

FIG. 9 illustrates an alternative embodiment 900 of a drawstring securing member 930 composed of a first securing member element 940 including a first hook shaped structure 990 and a second securing member element 941 including a second hook-shaped structure 991. Also shown is the first set of drawstrings 932 and the drawstring grasping region 995 between the first and second hook shaped structures 990, 991.

In operation, the embodiment of FIG. 9 performs substantially similarly to the embodiment of FIGS. 4-8.

Figure 10:
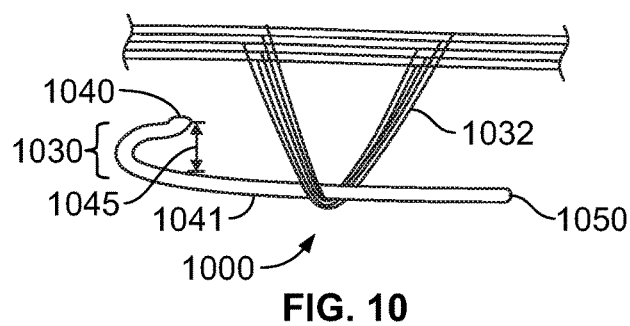
FIG. 10 illustrates an alternative embodiment of a drawstring securing member composed of an arcuate structure.

FIG. 10 illustrates an alternative embodiment 1000 of a drawstring securing member 1030 composed of an arcuate structure 1041. The arcuate structure 1041 is attached at a first end 1040 to the side of the waste bin and then arcs outwardly from the side of the waste bin in a generally horizontal plane. The distal end 1050 of the arcuate structure 1041 is not attached and is positioned outwardly from the side wall of the waste bin by a positioning distance 1045.

In operation, a set of drawstrings 1032 may be engaged with the arcuate structure 1041 by sliding the drawstrings onto the distal end 1050 of the arcuate structure.

Figure 11:
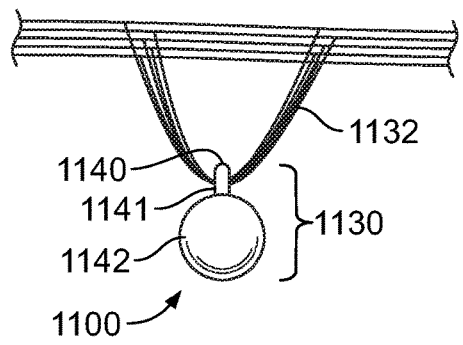
FIG. 11 illustrates an alternative embodiment of a drawstring securing member composed of rod having a bulbous end.

FIG. 11 illustrates an alternative embodiment 1100 of a drawstring securing member 1130 composed of a rod 1141 having a bulbous end 1142. The rod 1141 is attached at a first end 1140 to the side of the waste bin and then extends outwardly from the side of the waste bin in a generally horizontal plane.

In operation, a set of drawstrings 1132 may be engaged with the rod 1141 by sliding the drawstrings over the bulbous end 1142.

Figure 12:
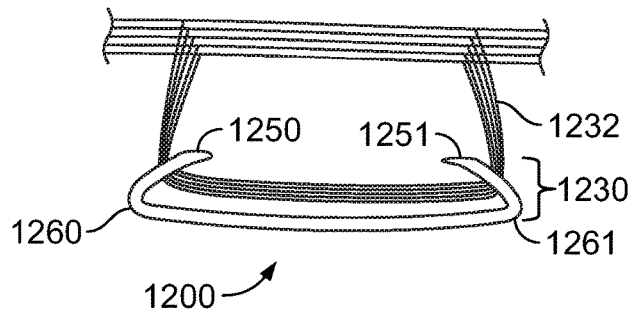
FIG. 12 illustrates an alternative embodiment of a drawstring securing member composed of a U-shaped structure where the base of the U is wider than the top.

FIG. 12 illustrates an alternative embodiment 1200 of a drawstring securing member 1230 composed of a U-shaped structure 1261 where the base of the U is wider than the top. The U-shaped structure 1261 is attached at its top to the side of the waste bin at a first U-top attachment 1250 and a second U-top attachment 1251. The U-shaped structure then extends outwardly from the side of the waste bin in a generally horizontal plane. The base of the U-shaped structure includes a first U-base lateral extent 1260 and a second U-base lateral extent 1261. The lateral distance between the first U-base lateral extent 1260 and second U-base lateral extent 1261 is greater than the lateral distance between the first U-top attachment 1250 and second U-top attachment 1251 and generally slopes uniformly inwardly toward the side wall of the waste bin.

In operation, a set of drawstrings 1232 may be engaged with the U-shaped structure 1261 by introducing the set of drawstring around the first U-base lateral extent 1260 and second U-base lateral extent 1261.

Figure 13:
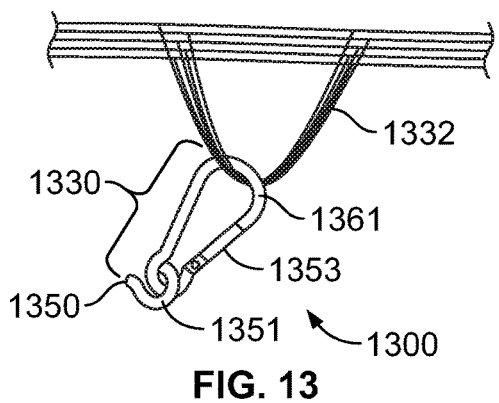
FIG. 13 illustrates an alternative embodiment of a drawstring securing member composed of a carabiner.

FIG. 13 illustrates an alternative embodiment 1300 of a drawstring securing member 1330 composed of a carabiner 1361. The carabiner 1361 is attached to a hook or loop 1351 that is attached to the side wall of the waste bin at attachment point 1350.

In operation, a set of drawstrings 1332 may be engaged with the carabiner 1361 by displacing the swing arm 1353 of the carabiner and introducing the set of drawstrings into the interior of the carabiner as shown in FIG. 13.

Figure 14:
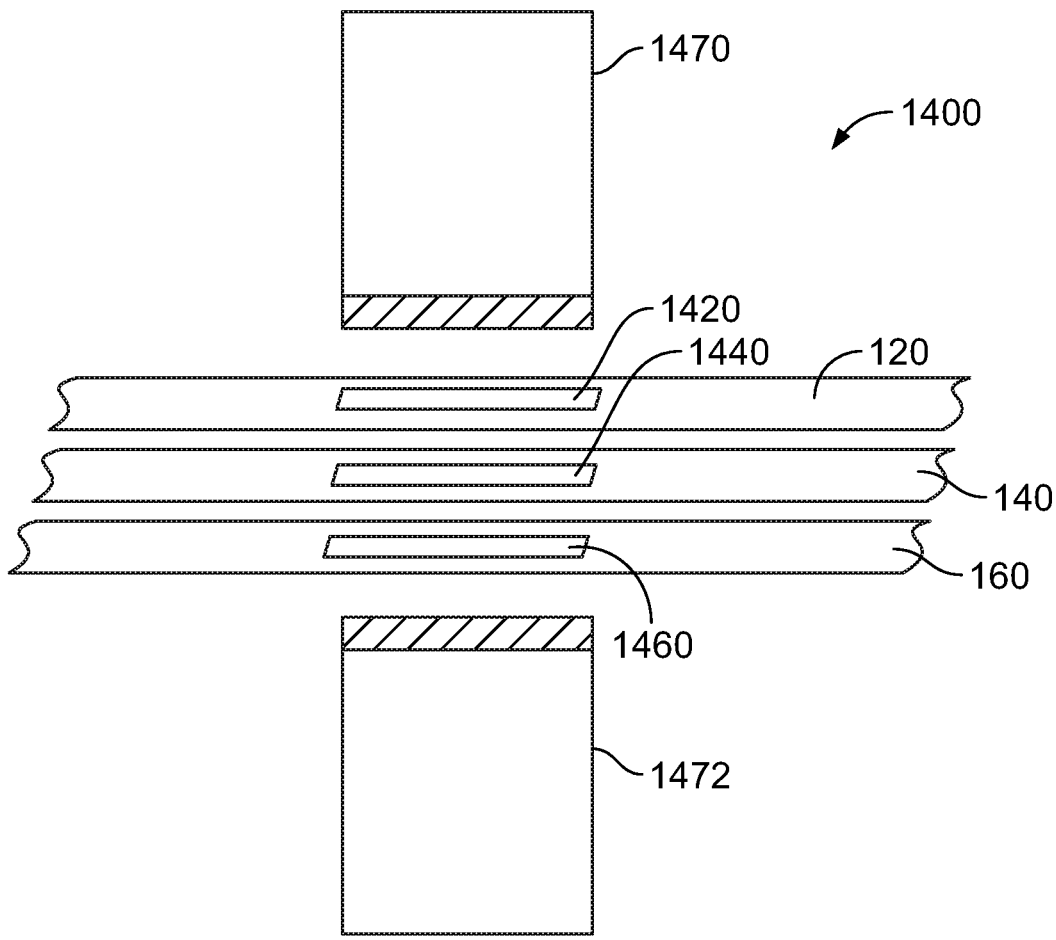
FIG. 14 illustrates an alternative embodiment of the drawstring joining member employing a thermally adhesive clamp.

FIG. 14 illustrates an alternative embodiment 1400 of the drawstring joining member employing a thermally adhesive clamp. As shown in FIG. 4, the exterior bag first drawstring 120, medial bag first drawstring 140, and interior bag first drawstring 160 are positioned on top of each other and in parallel. A thermal clamp including top clamp structure 1470 and bottom clamp structure 1472 is also shown. In operation, the top clamp structure 1470 and bottom clamp structure 1472 are induced together to clamp the drawstrings 120, 140, 160 between the clamp structures 1470, 1472. The clamp structures 1470, 1472 apply pressure and/or heat to the drawstrings 120, 140, 160 to cause the drawstrings 120, 140, 160 to thermally adhere to each other. The region of each drawstring that experiences the contact, pressure and/or heat of the clamp structure is called its adherence region including the exterior bag first drawstring adherence region 1420, medial bag first drawstring adherence region 1440, and interior bag first drawstring adherence region 1460. Similar thermal clamping may be employed on the exterior, medial, and interior second drawstrings.

Although the thermal clamp generally keeps the drawstrings physically connected, when a user wished to remove a bag from the waste bin 420, the user may separate one drawstring from the other drawstring to which it is clamped by inducing a force between the drawstrings sufficient to overcome the thermal adhesion of the drawstrings.

Figure 15:
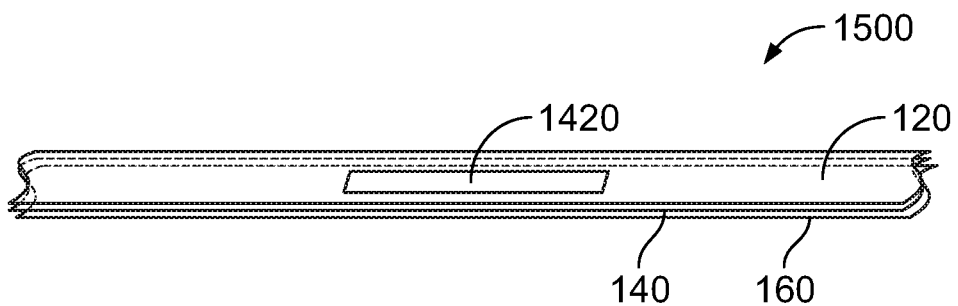
FIG. 15 illustrates the thermally clamped drawstrings of FIG. 14 in a clamped position.

FIG. 15 illustrates the thermally clamped drawstrings of FIG. 14 in a clamped position.

Alternatively, as mentioned herein, the joining member may be an adhesive that is positioned between one or more of the exterior, medial, and/or interior drawstrings. Alternatively, one or more of the exterior, medial, and/or interior drawstrings may be joined together by a structural element having perforations that may be torn to separate the drawstrings.

In one embodiment, the pre-loaded waste bag system includes a plurality of separate receptacles or waste bags, each having a drawstring disposed within a hem on the top portion of the bag, with openings to pull the drawstring on opposite ends. Each bag of the plurality of waste bags is nested one inside the other, with the drawstring openings aligned on each end. The drawstrings are pulled slightly through the openings and removably tied or connected together. Two pairs of securing members, either molded into opposite sides of a waste bin or adhered to opposite sides of a pre-existing waste bin, protrude on either side of the waste bin. Each pair of securing members includes two securing members placed a distance apart, creating a gap between the two securing members. The nested waste bags are placed inside the waste bin, the top edges of the waste bags containing the drawstrings placed around the rim of the waste bin, and the drawstrings looped around the corresponding securing members. When the drawstrings are looped around the securing members, the gap between the securing members creates a handle shape for easy access to and unsecuring of the drawstrings. The system is designed to be equally useful for residential or commercial use.

In one embodiment, a releasable, scented square is affixed to the nested waste bags in such a way that when the innermost waste bag is removed, the two sheets of the scented square separate, releasing a pleasant odor.

One or more embodiments of the present invention includes a pre-loaded waste bag system, which comprises a plurality of nested waste bags positionable within a waste bin and attachable to two pairs of securing members on opposite sides of a waste bin. The top edges of the front and back walls of each of the nested waste bags contain a generally tubular hem with a drawstring disposed within the hem. Openings exist on opposite sides of the hem, exposing the drawstring, allowing the drawstring to be pulled at each end, tightening the drawstring around the opening. In one embodiment, a releasable, scented square is affixed to each of the nested waste bags in such a way that when the innermost waste bag is removed, the two sheets of the scented square separate, releasing a pleasant scent or perfume.

In operation, the nested waste bags are placed inside the waste bin, the top edges of the waste bags are placed around the rim of the waste bin so that the hem is on the outer edge of the waste bin. The drawstrings are looped around the corresponding pairs of securing members attached to opposite sides of the waste bin. When the drawstrings are looped around the securing members, the gap between securing members causes the drawstrings to be positioned in a handle shape for easy access to and unsecuring of the drawstrings from the securing members.

While secured, the drawstrings reduce the likelihood of the nested waste bags shifting or falling into the waste bin by (i) serving as a connection between the nested waste bags and the securing members, holding the nested waste bags in position, and (ii) tightening the top edge of the nested waste bags around the waste bin as a greater load is added to the interior of the waste bags due to the tightening of the drawstrings. The tightened drawstring includes the frictional force between the waste bags and the waste bin to assist in maintaining the position of the waste bags.

To remove the innermost waste bag of the nested waste bags, the user grasps the corresponding drawstring portion made accessible by the gap between the securing members and removes the drawstring from the securing members by displacing the drawstring downward and outward to clear the securing members and then lifting the drawstring, thus allowing the innermost waste bag to be removed from the nested waste bags by vertically lifting the innermost waste bag away from the next waste bag so that the innermost waste bag may be disposed of. When the innermost waste bag is removed, the releasable, scented square is activated. The releasable scented square includes two sheets of pliable material releasably adhered together with a scent or perfume contained in the middle. The outer portion of each sheet of the scented square is adhered to either the inner side of a nested waste bag or the outer side of the next innermost waste bag.

In one embodiment, a waste bin capable of receiving and supporting the nested waste bags has at least one sidewall, an upper opening and a floor exposing an interior of the waste bin. The waste bin may take the shape of any variety of structures and arrangements, including a structure containing an upper edge or ring. The waste bin may also be comprised of various types of materials including, but not limited to, plastic, metal, wood, wicker, cardboard, carbon fiber, and/or composites of any of the preceding materials. The waste bin may be comprised of a permanent or disposable structure, for example an expandable or collapsible structure. One or more securing members may be installed upon the waste bin as further described below.

At least one pair of securing members is attached to the exterior of the waste bin's sidewall. A plurality of the pairs of securing members are preferably attached to the waste bin in various locations, including, but, not limited to, the outer sidewalls of the waste bin, providing additional support to the nested waste bags while receiving a load. One embodiment includes two pairs of securing members attached to opposite sides of the exterior of the waste bin's sidewall. Each pair of securing members is formed for extending through and securing the drawstrings of the nested waste bags thereby maintaining the upper portion of the nested waste bags overlapping the upper rim of the waste bin.

The drawstrings of the nested waste bags are initially and temporarily tied together using a joining element, such as a twist tie, so that the drawstrings may be looped around the securing members with one action. Once the drawstrings are looped around the securing members, the joining element is removed, allowing the drawstrings to be individually engaged and unlooped from the securing members so that the waste bags may be individually removed from the waste bin. Alternatively, as described in FIGS. 14 and 15, the drawstrings may be joined together using a thermally adhesive claim, adhesives between the drawstrings, and/or a perforated structure between the drawstrings, any of which are separable to allow a drawstring to be removed from the other drawstrings as the waste bag is removed.

Each pair of securing members may be comprised of various structures capable of extending through and securing the drawstring, including but not limited to the securing members having a v-shaped base member with two hook-shaped members in parallel alignment a distance from one another, creating the gap for the user to grasp and individually unsecure the drawstrings. An alternative embodiment may include hook-shaped members independent of a base member attached to the waste bin a distance apart, creating the gap. In the present embodiment, the base member may be attached to the waste bin using various attachment structures such as, but not limited to, fasteners, adhesive tape, glue, bonding material or molded directly into the waste bin.

Although in the exemplar embodiment described above, a pair of securing members is used, alternative embodiments may use a single securing member, three securing members, or a single bar that extends perpendicular to the outer sidewall of the waste bin and then horizontally parallel to the outer sidewall, creating a laterally extending bar to hook the drawstrings over. Alternative embodiments may also have the drawstrings looped around one or multiple small rods with bulbous ends, a u-shaped bar, or a carabiner. The securing members may be permanently or removably affixed by any number of methods, including but not limited to adhesive, velcro, magnets, clips, as well as being molded into the sidewalls of the waste bin. When multiple securing members are employed, the securing members may be placed on various locations around the sidewalls or upper rim of the waste bin to secure the waste bags. Securing members may be placed on one sidewall or on every sidewall with appropriate modifications to the waste bags so the drawstrings protrude through the hem in the appropriate locations.

The nested waste bags are formed by a plurality of individual waste bags positioned one inside the other. The nested waste bags are comprised of at least an inner bag and an outer bag and may include one or more medial bags between the inner bag and the outer bag. A set of nested waste bags may be comprised of any number of bags including, but not limited to, five, ten, fifteen or more.

When nested, each bag of the plurality of nested waste bags is nested one inside the other, with the drawstring openings aligned on each end. The drawstrings are pulled slightly through the openings, and removably attached to one another by an attaching structure such as twist ties, clamps, or clips, or adhered to one another using adhesive or a heated element. The removable attachment allows the nested waste bags and drawstrings to remain aligned during installation into the waste bin and when looping the drawstrings around the securing members.

In one embodiment, each bag of the plurality of nested waste bags is a rectangular bag having at least a front and a back wall. In alternative embodiments, the nested waste bags are given a variety of shapes to fit an assortment of waste bins, including but not limited to rectangular, cylindrical, hemispherical, and triangular. The front and a back walls are secured along their side edges and their bottom edge. The top edges of the front and back walls are left separate from each other and together define an opening into the interior of the bag. The top edges of the front and back walls contain a tubular or cylindrical hem with a drawstring disposed within the hem wherein the ends of the drawstring are adhered or attached to the hem, using adhesive or heat to bind the drawstring to the hem at approximately the midpoint of the waste bag so when the drawstring is engaged, it passes through the hem to constrict the opening of the bag. Openings exist on opposite sides of the hem, exposing the drawstring, allowing the drawstring to be pulled at each end, tightening the drawstring around the opening. Alternative embodiments may include a single opening or multiple openings corresponding to the number and location of securing members attached to the waste bin.

Each releasable, scented square is composed of two sheets, composed of a pliable material such as paper or plastic releasably adhered together or positioned proximally to one another with a seal around the perimeter and a scent or perfume contained in the middle of the inner side of the sheet.

Each sheet includes an inner and outer side, with the inner side adhered to the second sheet and the outer side adhered to the nested waste bag. The releasable scented square is applied to the nested waste bags so that the outer side of the first sheet of the scented square is adhered to the inner side of a nested waste bag and the outer side of the second sheet of the scented square is adhered to the outer side of the next innermost waste bag.

The inner side of the sheet has a substance that emits a pleasant scent or perfume, such as lavender, disposed in the middle of the inner side of the sheet. Each edge of the inner side of the sheet contains a releasable adhesive. The outer side of the sheet is coated with a permanent adhesive.

The releasable scented square is assembled by aligning the releasable adhesive edges of the two sheets, creating an airtight seal that prevents the scent or perfume from prematurely dissipating. The outer side of the first sheet is then affixed to the inner wall of a waste bag. By placing a second nested waste bag inside the first waste bag, the outer side of the second sheet becomes affixed to the outer wall of the second waste bag by contacting the adhesive on the outer side of the second sheet with the outer wall of the second waste bag.

When the innermost waste bag is removed from the waste bin, the releasable adhesive has been selected to provide an adhesion force that allows the two sheets to separate as the innermost waste bag is lifted away from its surrounding waste bag, thus exposing the inner side of the sheet to the air so that it releases the scent or perfume that will be carried with the innermost waste bag's outer wall as well as the surrounding waste bag's inner wall. An alternative embodiment may only have the scent or perfume disposed on the interior side of the sheet so that the scent or perfume remains with the surrounding waste bag's inner wall.

Although in the exemplar embodiment described above a perfume is used, alternative embodiments may use an antimicrobial or anti-bacterial substance, such as Lysol®, rather than, or in addition to, a perfume. Alternative embodiments may also have the scented square adhered only to the inner wall of the outermost bag and have the sheet peeled away manually exposing the perfume.

If the waste bin does not have pre-installed securing members, the user first affixes the securing members to the outer wall of the waste bin as described above.

The first step in installing the nested waste bags is to position the nested waste bags within the interior of the waste bin through the upper opening and the upper portion of the nested waste bags around the rim of the waste bin so that the hem is on the outer edge of the waste bin.

Next, the user aligns the drawstrings of the nested waste bags with the respective securing members. The user then loops the drawstrings around the securing members, securing the waste bags and creating a gap for later unsecuring. The user then removes the removable attachment binding together the drawstrings so that each waste bag may be individually unsecured and removed from the waste bin. The innermost waste bag now functions as a conventional garbage bag.

When the innermost waste bag needs to be removed from the waste bin, the user simply grasps the innermost waste bag's drawstring at the gap, pulls down to unsecure the drawstrings from the securing members, and then lifts the waste bag upward out of the waste bin. The action of pulling the innermost bag upward out of the waste bin separates the two sheets of the releasable, scented square, releasing a pleasant odor for both the waste bag that was removed as well as the next bag that now serves as the innermost waste bag inside the waste bin as described above. The user can continue this process until all of the nested waste bags in the set have been removed, at which point a new set of nested waste bags can be installed using the process described above.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:
1. A pre-loaded waste bag system including:
   a set of pre-loaded waste bags including
     a first waste bag having first waste bag first drawstrings and first waste bag second drawstrings;

a second waste bag having second waste bag first drawstrings and second waste bag second drawstrings,
wherein said second waste bag is positioned inside said first waste bag; and
a waste bin including:
a first drawstring securing member including a first drawstring engagement structure;
a second drawstring securing member including a second drawstring engagement structure,
wherein said first waste bag first drawstrings and said second waste bag first drawstrings engage with said first drawstring engagement structure,
wherein said first waste bag second drawstrings and said second waste bag second drawstrings engage with said second drawstring engagement structure,
wherein at least one of said first drawstring securing member and said second drawstring securing member includes a plurality of hook-shaped structures,
wherein drawstrings that are engaged with said plurality of hook-shaped structures form a grasping region between said hook-shaped structures.

2. The system of claim 1 wherein said waste bin includes a bag hem engagement structure that engages with at least one hem of said first waste bag and said second waste bag.

3. The system of claim 1 further including at least one drawstring joining member joining drawstrings of said first waste bag and said second waste bag.

4. The system of claim 1 further including at least one additional waste bag positioned between said first waste bag and said second waste bag, wherein said at least one additional waste bag includes additional waste bag first drawstrings that engage with said first drawstring engagement structure and additional waste bag second drawstrings that engage with said second drawstring engagement structure.

5. The system of claim 1 wherein at least one of said first drawstring engagement structure and said second drawstring engagement structure is an arcuate structure extending horizontally from the side of said waste bin.

6. A pre-loaded waste bag system including:
a set of pre-loaded waste bags including
a first waste bag having first waste bag first drawstrings and first waste bag second drawstrings;
a second waste bag having second waste bag first drawstrings and second waste bag second drawstrings,
wherein said second waste bag is positioned inside said first waste bag; and
a waste bin including:
a first drawstring securing member including a first drawstring engagement structure;
a second drawstring securing member including a second drawstring engagement structure,
wherein said first waste bag first drawstrings and said second waste bag first drawstrings engage with said first drawstring engagement structure,
wherein said first waste bag second drawstrings and said second waste bag second drawstrings engage with said second drawstring engagement structure,
wherein at least one of said first drawstring engagement structure and said second drawstring engagement structure is a carabiner.

* * * * *